United States Patent [19]

Kadaba et al.

[11] Patent Number: 4,582,827
[45] Date of Patent: Apr. 15, 1986

[54] PESTICIDAL DIPHENYLAZIRIDINES

[75] Inventors: Pankaja K. Kadaba; Douglas L. Dahlman, both of Lexington, Ky.

[73] Assignee: The University of Kentucky Research Foundation, Lexington, Ky.

[21] Appl. No.: 529,631

[22] Filed: Sep. 6, 1983

[51] Int. Cl.$^4$ .................... A01N 43/44; C07D 203/14
[52] U.S. Cl. ................................ 514/183; 260/239 E
[58] Field of Search .................... 260/239 AR, 239 E; 424/244; 514/183

[56] References Cited

U.S. PATENT DOCUMENTS

| | | | |
|---|---|---|---|
| 2,694,696 | 11/1954 | Melamed | 260/239 E X |
| 2,802,823 | 8/1957 | Tolkmith et al. | 260/239 R |
| 2,802,824 | 8/1957 | Tolkmith et al. | 260/239 R |
| 3,071,574 | 1/1963 | Brust | 260/239 EP |
| 3,285,909 | 11/1966 | Rabourn | 260/239 E |
| 3,297,682 | 1/1967 | Kuhn | 260/239 AR |
| 3,335,130 | 8/1967 | Kuhn | 260/239 E |
| 3,335,132 | 8/1967 | Kuhn | 260/239 E |

FOREIGN PATENT DOCUMENTS 809414  3/1937  France .

OTHER PUBLICATIONS

Eremeev, et al., Latv. PSR Zinat. Akad. Vestis, Kim. Ser., vol. 4, (1977), pp. 501–503.
Liepins, et al., Khim. Geterotsikl. Soedin., vol. 7, (1977), pp. 906–909.
Liepins, et al., Khim. Geterotsikl. Soedin., vol. 3, (1978) pp. 338–341.
Liepins et al, Chem. Abstracts, vol. 87:183795b (1977).
Eremeev et al, Chem. Abstracts, vol. 88:22491e (1978).
Liepins et al, Chem. Abstracts, vol. 89:41721s (1978).

Primary Examiner—Donald G. Daus
Assistant Examiner—William A. Teoli, Jr.
Attorney, Agent, or Firm—Lowe, Price, LeBlanc, Becker & Shur

[57] ABSTRACT

Substituted 1,2-diphenylaziridines, particularly those which are substituted by halogen, are useful as pesticidal compositions. These 1,2-diphenylaziridines are of the following formula:

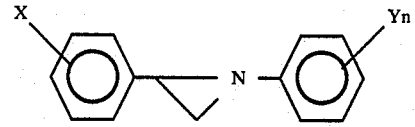

wherein X is selected from the group consisting of hydrogen, halogen, and nitro, and Y is selected from the group consisting of hydrogen, halogen, nitro, trifluoromethyl, and lower alkyl of 1–3 carbon atoms, and n is an integer of 1 or 2, provided that when one of X and Y is hydrogen or nitro, the other is halogen.

18 Claims, No Drawings

PESTICIDAL DIPHENYLAZIRIDINES

FIELD OF THE INVENTION

This invention relates to 1,2-diphenylaziridines and more particularly to 1,2-diphenylaziridines which are useful as pesticidal agents and which have low mammalian toxicity.

BACKGROUND ART

Many pesticides and insecticides are known to the art and are important in agriculture as tools for controlling insect pests. Many of the insecticides presently in use however, such as the organophosphorous compounds, the carbamates and the chlorinated hydrocarbons, while effective against insects, have very high mammalian toxicity and some of these materials are believed to have carcinogenic and teratogenic effects. At the present time the insecticidal situation in particular is becoming increasingly controversial because the past use of broad spectrum insecticides such as the chlorinated hydrocarbons to achieve maximum kill of pests, has resulted in excessive pollution of the environment. Moreover, the problem of pesticidal residues in crops with their attendant hazards to human health, the rapid development of insecticide resistant populations, severe effects on non-target species, and rapid changes in status of secondary pests, has created a situation where new pesticidal materials must be provided.

It will be understood that the philosophy of pest control is changing and the strategy now is an integrated approach to pest management utilizing biological, chemical and natural control factors. This approach employs the idea of maximizing natural control forces and using other tactics with a minimum of disturbance to the agro-economic system. Therefore it is important that the new pesticides be selective in their action rather than being the type of material which will achieve maximum kill of pests. Thus the importance of establishing minimum dosage rates for holding pest populations just below economic injury levels are now important.

SUMMARY OF THE INVENTION

It is accordingly one object of the present invention to provide new pesticidal compositions which have effective pesticidal activity and are very selective with respect to the insects, and at the same time have low oral mammalian toxicity and are not mutagenic.

A further object of the invention is to provide a new class of aziridine pesticidal compounds which have low mammalian toxicity and are not mutagenic.

A still further object of the present invention is to provide a new class of diphenylaziridine compounds which are particularly effective as insecticidal compositions and which are characterized by low mammalian toxicity and will provide a minimum of disturbance to the agro-economic system.

An even further object of the present invention is to provide a method for the control of pests and insects by application thereto of a new class of pesticidal 1,2-diphenylaziridines.

Other objects and advantages of the present invention will become apparent as the description thereof proceeds.

In satisfaction of the foregoing objects and advantages there is provided by this invention a new class of 1,2-diphenylaziridines which may be defined by the following general formula:

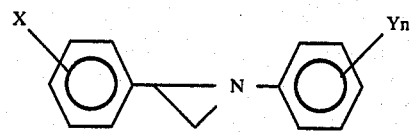

In the above formula, X is hydrogen, halogen or nitro and Y is hydrogen, halogen, nitro, trifluoromethyl, or lower alkyl of 1-3 carbon atoms and n is an integer of 1 or 2, provided that when one of X or Y is hydrogen or nitro, the other X or Y must be halogen.

Also provided by the present invention are pesticidal compositions which contain as the active ingredient, the 1,2-diphenylaziridines of the above formula. There is also provided by the present invention methods for the control of pests, and particularly insects, which comprises application to the pests of a pesticidal composition which contains the 1,2-diphenylaziridines of the above formula as the effective ingredient.

DESCRIPTION OF PREFERRED EMBODIMENTS

The present invention is concerned with a new class of aziridine compounds which have effective pesticidal activity with good selectivity. Further, the compounds and compositions of the present invention have low oral mammalian toxicity and are not mutagenic. Accordingly, the compositions of the present invention represent a class of pesticidal materials which are imminently useful in the new approach to pest management.

While a number of aziridine compounds have been reported as antimicrobial agents, such as aziridinylbenzoquinones and 1-aziridine carboxylic acid esters as fungicides and even as antibiotic and antitumor substances, none of these compositions have been suggested as pesticidal agents and none of these compositions involve 1,2-diphenylaziridines. Numerous aziridinyl phosphorous compounds have also been found to possess chemosterilant activity towards a number of insect species (Dermet et al, "Ethyleneimine and Other Aziridines", Academic Press, New York, 1969) including the tobacco budworm as reported by Flint et al, J. Econ. Entomol., 61, 939, 1968. However, aziridinyl phosphorous compounds are highly toxic to mammals and may also be carcinogenic and mutagenic as discussed by Dermet et al, and others.

It is therefore unexpected that the 1,2-diphenylaziridines of the present invention not only have good pesticidal activities but also are characterized by the low mammalian toxicity and are not mutagenic as shown by the Ames' test.

The 1,2-diphenylaziridines of the present invention are of the following general formula:

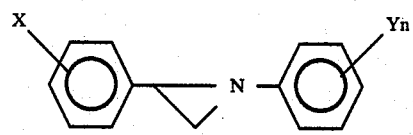

wherein in the above formula, X is hydrogen, halogen or nitro, and Y is hydrogen, halogen, nitro, trifluoromethyl, or lower alkyl of 1-3 carbon atoms and n is an integer of 1 or 2, provided that when one of X or Y is hydrogen or nitro, the other must be halogen.

Compounds of the present invention can be prepared from the corresponding 1,2,3-triazolines. Such triazolines are known in the prior art primarily through publications of one of the applicants. Thus the following publications describe procedures for the production of triazolines through cycloaddition of diazomethane to Schiff bases and solvent effects on this reaction as well as steric effects. (Kadaba, P. K., and Fannin, N., Journal of Heterocyclic Chemistry, 4, 1967, pp. 301-304.) (Kadaba, P., Journal of Heterocyclic Chemistry, 6, 1969, pp. 587-589.) (Kadaba, P. K., "Synthesis," International Journal of Methods in Synthetic Organic Chemistry, No. 2, February 1973, pp. 71-84.) (Kadaba, P. K., Journal of Heterocyclic Chemistry, 12, 1975, pp. 143-146.) (Kadaba, P. K., Journal of Heterocyclic Chemistry, 13, 1976, pp. 1153-54).

In preferred procedures, the triazoline intermediates used in this invention may be prepared by the reaction of diazomethane with Schiff bases as described, for example, by Mustafa, A., J. Chem. Soc., 234 (1949), and by Buckley, G. D., J. Chem. Soc., 1850 (1954). Further methods of preparation involving 1,3-dipolar cycloaddition reactions are described in the applicants' own publication in Kadaba, et al., J. Org. Chem., 26, 2331 (1961); by Kadaba in "Tetrahedron," 22, 2453 (1966), and by Kadaba in "Tetrahedron," 25, 3053 (1969). This reaction proceeds generally in accordance with the following equation:

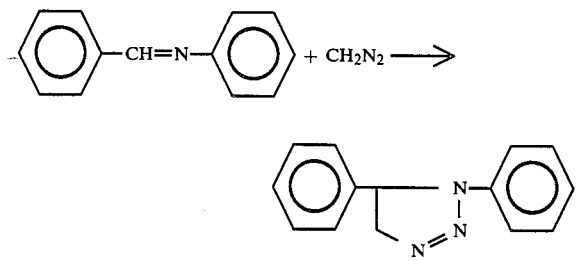

Since Schiff bases (imines) bearing a range of aromatic or heterocyclic substituents can be readily prepared, the $CH_2N_2$-imine reaction is particularly suited for the synthesis of the 1,5-substituted triazolines. In a typical preparation, the Schiff base is dissolved in a cold, freshly prepared solution of $CH_2N_2$ in wet dioxane. The reaction mixture is then allowed to stand at 15°-20° C. for 2-4 days in the case of the reactive anils and 6-7 days in the case of the slow reactions. At the end of this period, the mixture is cooled and diluted with water to precipitate the triazoline adduct.

It has been discovered in accordance with the present invention that triazolines of this type undergo decomposition, when irradiated with ultraviolet light to provide either aziridines as the sole product or aziridines mixed with minor amounts of imines depending on the structure of the triazoline starting material. Thus the preferred method of production of the compounds of the present invention is by photolysis of 1-diphenyltriazolines in accordance with the following equation:

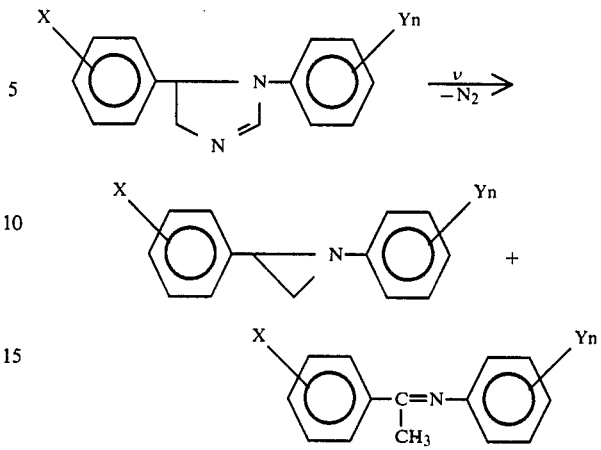

In the above equation, X, Y and n are as described above. Further, in this equation it will be noted that the 1,5-diphenyltriazoline decomposes in accordance with the process of this invention to produce a major amount of the product of this invention, 1,2-diphenylaziridine, and a minor amount of the imine.

In a typical experiment for the preparation of the products of the invention, the triazoline is photolyzed in a facile reaction by irradiation of the triazoline in acetone solution using a 275 watt GE sunlamp as the light source. The photodecomposition reaction proceeds at a reasonably fast rate and does not necessitate the use of an internal ultraviolet light source. The resulting aziridine products are characterized by their NMR spectra which show two closely similar doublets for the 2-CH proton in the region $\delta 3$-4 and a multiplet of 8 peaks for the 3-$CH_2$ protons in the $\delta 2$-3 region.

The most preferred compounds according to the present invention are those wherein X is halogen in the ortho position on the 2-phenyl ring and Y is halogen or trifluoromethyl in the para position on the 1-phenyl ring. Particularly preferred compounds are those wherein X is ortho-chloro and Y is para-bromo, X is ortho-chloro and Y is para-chloro, X is ortho-chloro and Y is para-trifluoromethyl, and X is ortho-fluoro and Y is para-fluoro. Other compounds of particular interest are those wherein X is ortho-chloro and Y is 3,4-dichloromethyl, and X is ortho-chloro and Y is para-fluoro.

As pointed out above, it was found that these compounds exhibit substantial pesticidal activity and particular insecticidal activity with different degrees of activity against different pests. The pesticidal compounds of the present invention may be applied in accordance with general procedures for the preparation of pesticidal compositions and their application to the insects. Thus, the compositions can be formulated in a conventional manner in the form of solutions, suspensions, emulsions, powders, or granules, depending on the selected application. Concentrations may range from about 10-5000 ppm or higher, and using a pesticidal effective amount. Preferably produced are aqueous compositions, but when powders or granules are desired, inert fillers will also be employed. Further, the compositions of the invention may be incorporated into insect foods on which the insects will feed but conventionally this would be by spraying of compositions of the invention onto crops and the like.

It has been found that the compositions of the present invention have at least a degree of pesticidal activity against the following pests:

Tobacco hornworm (*Manduca sexta*), tobacco budworm (*Heliothis virescens*), eastern tent caterpillar (*Malacosoma americanum*), salt-marsh caterpillar (*Estigmene acrea*), fall webworm (*Hyphantria cunea*), European corn borer (*Ostrinia nubilalis*), Japanese bettle (*Popillia japonica*), spined soldier bug (*Podisus maculiventris*), house fly (*Musca domestica*), face fly (*Musca autumnalis*), American cockroach (*Periplaneta americana*), German cockroach (*Blattella germanica*), and *Blaberus discoidalis*, a cockroach without a common name used in laboratory studies.

The following examples are presented to illustrate the invention but are not to be considered as limiting thereon. In the following examples and throughout the specification, parts are by weight unless otherwise indicated.

EXAMPLE 1

Using the procedure described above for photolysis of the corresponding 1,5-triazoline, substituted 1,2-diphenylaziridines of the following formula were prepared:

| Compound No. | X | Y |
|---|---|---|
| 1 | o-Cl | p-Br |
| 2 | o-NO$_2$ | 3,4-diCl |
| 3 | o-NO$_2$ | m-NO$_2$ |
| 4 | m-NO$_2$ | H |
| 5 | o-Cl | H |
| 6 | H | p-Br |
| 7 | H | H |
| 8 | m-Cl | p-Br |
| 9 | p-Cl | p-Br |
| 10 | o-Cl | 3,4-diCl |
| 11 | o-Cl | p-Cl |
| 12 | o-Cl | m-Cl |
| 13 | o-Cl | p-F |
| 14 | o-Cl | p-CF$_3$ |
| 15 | o-F | p-F |
| 16 | o-Cl | p-Et |

EXAMPLE 2

The compounds produced and described in Example 1 were then tested for pesticidal activity against the tobacco hornworm (*Manduca sexta*). The screening procedure for these tests began with the larval stage and continued through the pupal and adult stages and finally evaluated egg production. The studies thus permitted the evaluation of the effects of the compounds over several subsequent developmental stages in the total life cycle of the insect, giving estimates of acute toxicity (insecticidal or larvicidal activity) as well as prolonged or delayed effects on development (growth regulation) and reproduction (chemosterilization). The latter are of special importance in conjunction with the integrated pest management approach to insect control.

The test compounds were incorporated into the artificial diet of tobacco hornworm larvae and their subsequent growth and developmental responses were monitored using the following parameters: larval mortality including determination of LD$_{50}$ values, rate of larval development and weight gain, percent pupation, pupal weight and degree of deformities, percent adult emergence and measures of reproductive capacity such as the number of developed ooctyes, fecundity and fertility. The protocol for the screening tests has been developed over a number of years by Dahlman et al., Comp. Biochem. Physiol. 51A, 33, (1975); Comp. Biochem. Physiol., 52A, 105 (1975); Ent. Exp. et Appl., 22, 123 (1977); Palumbo and D. L. Dahlman, J. Econ. Entomol. 71, 674 (1978); D. L. Dahlman, Ent. Exp. et Appl., 24, 327 (1978).

Each treatment used 15 newly ecdysed fifth-instar larvae. Death of larvae within a few hours to several days of initial exposure was considered to be acute toxicity. However, the compounds may reduce the maximum size attained by larvae and/or may retard growth so that larvae require additional time to attain their maximum size. Developmental parameters subsequent to the feeding stage also may be affected. For example, insects may fail to pupate, the pupae may be of small size or may possess malformations. Mortality may occur in the pupal stage or emerging adults may have wrinkled wings or other deformities. The number of eggs produced by treated females may be reduced and/or unfertile. Although acute toxicity is desirable in the control of any insect, the delayed effects which result in poor survival and reduced reproductive capacity are significant factors in the long-range program of pest management systems.

Several of the 1,2-diphenylaziridines tested produced one or more of these phenomena in the tobacco hornworm (see Tables I and II, following). Of the aziridine compounds screened, four demonstrated acute insecticidal activity and an additional eight showed significant activity in delaying development and reducing reproductive capacity. All compounds possessing acute insecticidal activity bear an ortho substituent on the C-phenyl ring of I (x=o-Cl or o-F and y=p-Br, p-Cl, p-F or p-CF$_3$.

Continuous cultures of *M. sexta* are maintained according to the procedures of Yamamoto, J. Econ. Entomol., 62, p. 1427 (1969). Ingredients of the diet formulation include sugar, casein, wheat germ oil, cholesterol, salt mixture, yeast, vitamins, antioxidants and fungal inhibitors, such as ascorbic acid, sorbic acid, formaldehyde and methyl-p-benzoate. All are incorporated into a liquid agar base which, when poured into holding pans, solidifies to form an adequate substrate upon which the insect larvae feed. Nearly any test material can be uniformly incorporated into such a diet. Thus, exposure to experimental compounds can be evaluated during all or any part of the larval stage. In addition, chronic or long-term effects in subsequent life stages can also be monitored.

The results from these studies, in which the 1,2-diphenylaziridines of Example 1 were incorporated singly into the diet of *M. sexta* at a concentration of 5 mM are presented in the following Table I.

TABLE I

Tobacco hornworm growth and developmental responses to feeding in last instar on diets containing 5 mM of various aziridine compounds.[a]

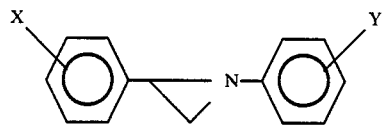

| Compound No. | X | Y | Max Larval Wt (g) | Days to Max Wt | % Pupation | % Adult Emergence | Total No. of Adults | % Malformed Adults | No. of ♀ Adults | Mean No. of Eggs |
|---|---|---|---|---|---|---|---|---|---|---|
| Control | | | 9.62 ± .27 | 5.2 ± .4 | 87 | 87 | 13 | 8 | 9 | 103 ± 15 |
| 1 | o-Cl | p-Br | ALL DEAD BY SECOND DAY OF FEEDING | | | | | | | |
| 2 | o-NO₂ | 3,4-diCl | 8.58 ± .31 | 6.2 ± .1 | 93 | 47 | 7 | 71 | 5 | 83 ± 29 |
| 3 | o-NO₂ | m-NO₂ | 9.21 ± .24 | 5.2 ± .1 | 100 | 80 | 12 | 8 | 9 | 97 ± 14 |
| 4 | m-NO₂ | H | 9.01 ± .17 | 5.1 ± .1 | 100 | 100 | 15 | 7 | 9 | 67 ± 16 |
| 5 | o-Cl | H | 5.42 ± .42 | 7.3 ± 1.4 | 40 | 40 | 6 | 17 | 3 | 14 ± 17[b] |
| 6 | H | p-Br | 4.83 ± .42 | 9.2 ± .5 | 53 | 47 | 7 | 27 | 5 | 7 ± 5[c] |
| 7 | H | H | 9.29 ± .17 | 6.7 ± .2 | 100 | 80 | 12 | 0 | 10 | 79 ± 19 |
| 8 | m-Cl | p-Br | 4.84 ± .19 | 7.8 ± .6 | 60 | 53 | 8 | 50 | 4 | 1 ± 0[c] |
| 9 | p-Cl | p-Br | 6.46 ± .23 | 5.0 ± .0 | 93 | 86 | 13 | 15 | 7 | 74 ± 14 |
| 10 | o-Cl | 3,4-diCl | 5.69 ± .27 | 7.5 ± .3 | 80 | 7 | 1 | 100 | 1 | 55 ± 0 |
| 11 | o-Cl | p-Cl | ALL DEAD WITHIN 24 HR OF START OF TEST | | | | | | | |
| 12 | o-Cl | m-Cl | 5.96 ± .40 | 7.6 ± .8 | 60 | 47 | 7 | 57 | 2 | 8 ± 11 |
| 13 | o-Cl | p-F | 6.13 ± .62[d] | 10.0 ± 4.2 | 13 | 13 | 2 | 50 | 0 | — |
| 14 | o-Cl | p-CF₃ | ALL DEAD WITHIN 3 DAYS | | | | | | | |
| 15 | o-F | p-F | 8.04 ± .41 | 6.7 ± .4 | 67 | 60 | 9 | 0 | 3 | 67 ± 42[e] |
| 16 | O—Cl | p-ET | 7.48 ± .31 | 5.5 ± .2 | 87 | 80 | 12 | 20 | 4 | 44 ± 20[e] |

[a] All tests began with 15 larvae
[b] Two had no eggs.
[c] Three had no eggs.
[d] 60% of larvae dead by day 2, only 13% pupated, essentially no weight gain for 4 or more days of larvae surviving that long.
[e] One had no eggs.

From Table I, it will be seen that Compounds 1, 11 and 14 produced similar symptoms but all larvae which fed on 11 were dead within 24 hours whereas 48 hours or more were required for those on the 1 and 14 diet. The symptoms included extreme agitation of larvae, oral and anal expulsion of fluids and ultimately, death. Although the mode of action in insects is presently unknown, the behavior of larvae suggests a neurological site of attack. In the case of Compound 13, 60% of larvae were dead by day two, and only 13% pupated. There was also no weight gain for 4 or more days for larvae surviving that long. In all 4 compounds, the Y function of structure in Example 1 is a para-substituent, Br for Compound 1, Cl for Compound 11, F for Compound 13 and CF₃ for Compound 14 and the X function in all 4 compounds is o-Cl.

Compounds 5, 6, 8 and 9 were tested with the primary objective of determining how structural changes in Compound 1 modified the activity. The results indicate that an ortho chloro substituent is necessary for larvicidal activity as in Compound 1. When the Cl is moved to the meta or para position, as in 8 and 9, or when absent, as in 6, potency decreased, 1>6~8>9.

Six other compounds, 5, 6, 8, 9, 10 and 12 caused significant (30–50%) reduction in the maximum weight of hornworm larvae. All but 9 extended the feeding time required for larvae to attain their reduced maximum weight.

Compounds 5, 6, 8 and 12, in addition to their inhibitory effect on larval growth, also caused significant larval mortality and a reduction in percent pupation.

Although percent adult emergence in 5, 6, 8 and 12 treated individuals was significantly lower than controls, the actual mortality occurred in the larval stage (see percent pupation). However, Compounds 2 and 10, both of which have a 3,4-dichloro substituent on the 1-phenyl, had significant pupal mortality. This would suggest a different mode of action on target sites.

Wrinkled or crumpled wings, which render the adult immobile or restrict its movements, were observed in significant numbers of moths from 2, 6, 8, 10, 13 and 12. The first five compounds have in common a halogen atom in the p-position of 1-phenyl, and 12 has a halogen in the m-position.

Of those compounds which permitted development to the adult stage, four (5, 6, 8 and 12) significantly reduced the mean number of eggs found in 4 day old females. These females had either very few eggs or none at all. While 5 and 6 have only a single halogen substituent, 8 has a p-bromo on the 1-phenyl (similar to 1) and a m-chloro on the 2-phenyl (unlike 1) of the aziridine ring.

Subsequent tests with various concentrations of Compounds 1, 11, 13 and 14 also demonstrated that the tobacco hornworm growth and developmental responses are concentration dependent as shown in Table II. While all or nearly all larvae died at 5 mM, 2.5 mM levels of all four compounds reduced maximum larval weight and the mean number of eggs. In addition, Compounds 1 and 11 lowered the percent pupation; Compound 14 caused 85% pupal mortality and a large percentage of the adults from Compounds 1 and 14 were malformed. At the 1 mM level, a slight reduction in larval weight was observed for Compounds 1 and 11 and the mean number of eggs was only half that of the controls for Compound 1. Lower concentrations had no apparent effects. Table II is as follows:

TABLE II

Tobacco hornworm growth and developmental responses to feeding in last instar on diets containing various azirdine compounds.

| Compound No. | X | Y | Max Larval Wt (g) | Days to Max Wt | % Pupation | % Adult Emergence | Total No. of Adults |
|---|---|---|---|---|---|---|---|
| Control | | | 9.62 ± .27 | 5.2 ± .4 | 87 | 87 | 13 |
| 2.5 mM in diet | | | | | | | |
| 1 | Cl | Br | 4.99 ± .29 | 6.2 ± 0.7 | 27 | 100 | 4 |
| 11 | Cl | Cl | 6.77 ± .32 | 7.7 ± 0.6 | 60 | 100 | 9 |
| 13 | Cl | F | 8.03 ± .25 | 8.7 ± 0.5 | 100 | 86 | 12 |
| 14 | Cl | CF$_3$ | 8.03 ± .47 | 6.6 ± 0.2 | 93 | 8 | 1 |
| 1 mM in diet | | | | | | | |
| 1 | Cl | Br | 7.94 ± .27 | 5.8 ± .2 | 100 | 100 | 15 |
| 11 | Cl | Cl | 8.29 ± .28 | 5.9 ± .1 | 100 | 100 | 14 |
| 13 | Cl | F | 9.50 ± .22 | 6.7 ± .2 | 100 | 100 | 15 |
| 14 | Cl | CF$_3$ | 9.20 ± .37 | 5.8 ± .1 | 93 | 100 | 14 |

| Compound No. | % Adults | % Malformed Adults | No. of ♀ Adults | Mean No. of Eggs |
|---|---|---|---|---|
| Control | | 8 | 9 | 103 ± 15 |
| 1 | 27 | 50 | 2 | 8 ± 9 |
| 11 | 60 | 0 | 7 | 15 ± 7 |
| 13 | 86 | 0 | 9 | 21 ± 9 |
| 14 | 7 | 100 | 1 | 0 |
| 1 | 100 | 0 | 10 | 32 ± 9 |
| 11 | 100 | 7 | 4 | 74 ± 22 |
| 13 | 100 | 7 | 11 | 71 ± 8 |
| 14 | 93 | 36 | 9 | 83 ± 13 |

The effects of lower concentrations were not different from controls.

From the results of Tables I and II, the structure activity relationships of the effects of 1,2-diphenylaziridines on the tobacco hornworm development could be stated as follows:

1. Compounds containing a p-Br, p-Cl, p-F or p-CF$_3$ on the 1-phenyl and an o-Cl on the 2-phenyl (Compounds 1, 11, 13 and 14) cause acute toxicity (100% larval mortality in 24–72 hours).
2. A p-Br on 1-phenyl or an o-Cl on 2-phenyl, by itself, or a combination of p-Br on 1-phenyl and m-Cl on 2-phenyl, (Compounds 6, 5 and 8) or m-Cl on 1-phenyl and o-Cl on 2-phenyl (Compound 12) caused reduction in maximum larval weight, percent pupation, and mean number of eggs, and an increase in malformed adults.
3. Compounds containing a 3,4-dichloro (Compounds 2 and 10) or a p-CF$_3$ (Compound 14) on 1-phenyl caused pupal mortality.
4. Unsubstituted 1,2-diphenylaziridine had no effect (Compound 7). Also compounds bearing m-NO$_2$ alone on 2-phenyl (Compound 4) or m-NO$_2$ on 1-phenyl and o-NO$_2$ on 2-phenyl (Compound 3) had no effect.

EXAMPLE 3

Those compounds of Example 2 demonstrating good oral activity (Compounds 1, 10, 11, 13, 14) were selected for topical studies. The test compounds were dissolved either in acetone or hexane and applied to the integument of the test insect with a micro applicator. Newly ecdysed fifth-instar tobacco hornworm larvae weighing between 1–1.5 g were used and toxicity data were obtained in the same way as previously described.

Of the compounds tested, Compound 13 had the greatest topical activity against the tobacco hornworm. A dose of 125 μg/larva(100 μg/g or 100 ppm) resulted in 60% mortality within 24 hr. Doses of 50 and 25 ppm caused reduced larval size and smaller number of eggs.

A treatment of 250 μg/larva of Compound 15 resulted in 100% mortality within 24 hr. but 125 μg/larvae killed only 20% during the entire 5th instar. However, the surviving larvae were smaller than controls.

Compound 11 was less active than Compound 13, but a dose of 500 μg/larva (400 ppm) killed 80% of the larvae within 48 hr. and a dose of 250 ppm resulted in 30% larval mortality, increased larval developmental time, reduced maximum weight and fewer numbers of eggs produced by the female moths.

A dose of 1000 μg/larva (800 ppm) of Compound 1 was necessary to kill 70% of the larvae within 48 hr; however, 400 ppm delayed larval development, reduced maximum size and the number of resulting eggs.

Compounds 10 and 14 were ineffective even at 2000 μg/larvae (1600 ppm).

Compounds 1, 10, 11, 13 and 14 were incorporated into H. virescens diet in the same manner as M. Sexta. Diets containing as much as 20 mM of each compound had little effect on larval development time, pupal weight or time to adult emergence.

A dose of 1500 ppm of Compound 13 applied to 200 mg 5th instars produced some of the symptoms characteristic of this group of compounds but failed to kill any of the larvae.

When Compound 15 was applied topically to 100 mg weight H. virescens larvae in a dose of 62.5 μg/larva or 625 ppm, it killed 60% within 48 hr.; 312 ppm of Compound 15 killed 40% within 48 hr.

EXAMPLE 4

Preliminary tests with topical applications of Compound 13 have been conducted on a number of insect species representing 5 different orders. Data were obtained in Table III. Since the same amount of compound was used, regardless of body size, the smaller species received a larger dose/body mass. More extensive work will be required to establish LD$_{50}$ values. However, the data demonstrates the potential effectiveness of Compound 13 against a number of economically important insects from different insect orders. Table III is as follows:

TABLE III

Topical Application Studies Using Compound 13

| Species | Order | Approx. Size (mg) | Dose (μg/g) | Result |
|---|---|---|---|---|
| Malacosoma americanum (larvae) | Lepidoptera | 500 | 1000 | 100% mortality w/in 24 hr |
| Estigmene acrea (larvae) | Lepidoptera | 800 | 1250 | 33% mortality w/in 24 hr |
| Hyphantria cunea (larvae) | Lepidoptera | 100 | 5000 | 50% mortality w/in 24 hr |
| Ostrinia nubilalis (larvae) | Lepidoptera | 80 | 6250 | No effect* |
| Popillia japonica (larvae) | Coleoptera | 250 | 500 | 100% mortality w/in 24 hr |

TABLE III-continued
Topical Application Studies Using Compound 13

| Species | Order | Approx. Size (mg) | Dose (μg/g) | Result |
|---|---|---|---|---|
| Musca domestica (Adult) | Diptera | 20 | 25,000 | 100% mortality 2/in 1.5 hr |
| Musca autumnalis (Adult) | Diptera | 20 | 25,000 | 100% mortality w/in 2 hr |
| Podisus maculiventris (nymphs & adults) | Hemiptera | 50 | 10,000 | 100% mortality w/in 1.2 hr |
| Periplaneta americana (adult) | Orthoptera | 750 | 666 | 100% mortality w/in 24 hr |
| Blattella germanica (adult) | Orthoptera | 70 | 7150 | 100% mortality w/in 24 hr |
| Blaberus discoidalis (nymphs) | Orthoptera | 500 | 1000 | 100% mortality w/in 24 hr |

*Nearing pupation size at time of treatment.

Although the compounds possess different levels of insecticidal activity, the toxicological symptoms associated with poisoning have a number of common characteristics, whether administered orally or topically. The delay in initial response was concentration dependent and for those insects treated with excessively high doses (i.e., the Musca spp.), it was not possible to observe these symptoms because of the rapid death. Lepidoptera larvae show initial responses of regurgitation and characteristic unnatural positioning of the abdomen which describes sharp bends, rather than the normal cylindrical shape. This is followed by convulsions and extreme writhing movements, and in some cases rectal prolapse and ultimately death.

The cockroaches first showed twitching and jerking movements of the abdomen and appendages, then became hyperactive before turning over on their backs. Leg twitching and other movements continued for some time before the insects became motionless.

The following conclusions with regard to possible modes of action can be drawn.
1. The action is probably not a direct CNS inhibition because of the intermediate speed of action.
2. A metabolite of the original compound must be produced and this is the active agent, or
3. Time is required to disperse the original material to the site of action.

In these studies, it has been determined that the 1,2-diphenylaziridines of this invention have low mammalian toxicity. Measurements of $LD_{50}$ values in acute oral toxicity tests using the rat, shows for example, that 1-(3-4-dichlorophenyl)-2-(2-chlorophenyl)aziridine (Compound 10) has an oral $LD_{50}$ value >2000 mg/kg.

Immediate effects, resulting from insecticide toxicity, are usually related to the principal toxic action of the compound. $LD_{50}$ values, obtained from conventionl acute oral toxicity test on rats, have proved to be a reliable index to assess whether the compound is safe to be used as an insect toxicant without causing danger to human health.

The high mammalian toxicity attributed to certain aziridine compounds is usually associated with the numerous aziridinyl phosphorus compounds, (Dermer et al, "Ethylenimine and Other Aziridines", Academic Press, New York, 1969), including tepa [tris(1-aziridinyl)-phosphine oxide] and metepa [tris(2-methyl-1-aziridinyl)phosphine oxide], which have been reported by a number of investigators to have carcinogenic and mutagenic properties. Simple ethyleneimine itself, and several compounds incorporating ethylenimine through its 1-position (similar to the bonding in Tepa and Metepa), as well as acylated aziridines and the aziridinium ion, are also highly toxic and hazardous, the toxicity being related to the number of aziridine rings present per molecule.

Standard Ames assay procedures have indicated that each of the aziridines (Compounds 1, 10 and 11) is not mutagenic either by itself or in the presence of mammalian liver enzymes (Table IV). This means that aziridine compounds, 1, 10, or 11, will not cause mutations in DNA arising from potential changes in frame shift and/or base pairing. Compounds 1, 10 and 11 were tested for mutagenic properties using the following experimental procedure.

Potential mutagenic and carcinogenic properties of the compounds were evaluated with standard Ames assay procedures (Ames et al, "Mutation Res.", 31, p. 347, 1975). This assay used strains of *Salmonella typhimurium* selected for sensitivity and specificity in being reverted from a histidine requirement back to prototrophy by a wide variety of mutagens. Potential changes in frameshift were evaluated using strains TA 98, TA 1537 and TA 1538, while changes in base pairing were detected using strains TA 100 and TA 1535. In addition, strain TA 1978 was used, in combination with TA 1538, to evaluate whether the agent killed bacteria by damage to DNA that could be repaired by this strain. Initially, the compounds were screened using the spot test, in which 1000 μgm of material dissolved in 10 μl of DNSO was applied to the middle of the plate. Results obtained were negative in all three cases as shown in the following Table IV.

TABLE IV
Mean Number of Revertant *Salmonella typhimurium* colonies per plate ± S.E. (Ames Assay)

| Strain | 1 +S9 | 1 −S9 | 10 +S9 | 10 −S9 | 11 +S9 | 11 −S9 |
|---|---|---|---|---|---|---|
| TA 98 ± | 44.0 | 32.7 | 45.3 | 26.7 | 44.7 | 27.3 |
| S.E. | 6.4 | 4.1 | 4.8 | 1.8 | 5.4 | 3.6 |
| TA 100 ± | 61.7 | 25.3 | 56.0 | 26.3 | 58.3 | 28.0 |
| S.E. | 3.9 | 2.0 | 3.9 | 4.7 | 3.0 | 5.5 |
| TA 1535 ± | 15.0 | 17.3 | 20.3 | 25.0 | 15.3 | 16.3 |
| S.E. | 1.4 | 2.5 | 4.8 | 5.1 | 2.9 | 0.4 |
| TA 1537 ± | 13.3 | 7.5 | 13.7 | 9.0 | 13.7 | 9.7 |
| S.E. | 1.5 | 2.7 | 0.8 | 0.7 | 2.2 | 1.5 |
| TA 1538 ± | 26.7 | 12.0 | 35.7 | 12.0 | 26.0 | 13.3 |
| S.E. | 1.5 | 1.2 | 3.2 | 5.8 | 5.4 | 4.2 |
| TA 1978 ± | 189.0 | 207.3 | 202.0 | 196.0 | 196.0 | 209.7 |
| S.E. | 13.6 | 20.4 | 4.2 | 16.2 | 16.2 | 10.8 |

| Strain | AAF +S9 | AAF −S9 | DMSO +S9 | DMSO −S9 |
|---|---|---|---|---|
| TA 98 ± | 284.7 | 32.7 | 40.0 | 28.0 |
| S.E. | 9.1 | 5.0 | 3.5 | 8.6 |
| TA 100 ± | 78.0 | 25.3 | 60.7 | 22.6 |
| S.E. | 1.9 | 2.2 | 7.2 | 3.8 |
| TA 1535 ± | 19.7 | 15.7 | 16.3 | 17.7 |
| S.E. | 2.3 | 2.2 | 2.7 | 3.3 |
| TA 1537 ± | 14.7 | 7.7 | 11.3 | 3.3 |
| S.E. | 0.4 | 2.2 | 3.6 | 1.5 |
| TA 1538 ± | 313.7 | 14.7 | 32.3 | 15.3 |
| S.E. | 45.0 | 1.5 | 6.6 | 1.6 |
| TA 1978 ± | 358.3 | 196.3 | 188.3 | 201.7 |
| S.E. | 18.9 | 16.0 | 30.4 | 12.8 |

Dose-response tests were not performed because the results were negative. All the tests were carried out in the presence and absence of an S9 rat liver preparation and contained a positive control (2-acetylaminofluorene, AAF) and a negative control (DMSO).

The invention has been described herein with reference to certain preferred embodiments. However, as obvious variations thereon will become apparent to those skilled in the art, the invention is not to be considered as limited thereto.

What is claimed is:

1. A compound of the following general formula:

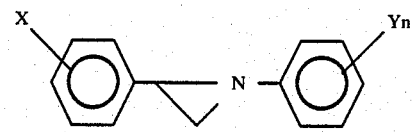

wherein X is selected from the group consisting of halogen in the ortho position, and nitro, and Y is selected from the group consisting of halogen, nitro, trifluoromethyl, and lower alkyl of 1-3 carbon atoms, and n is an integer of 1 or 2 provided that when one of X and Y is nitro, the other is halogen.

2. A compound according to claim 1 wherein X is halogen in the ortho position and Y is halogen or trifluoromethyl in the para position and n is 1.

3. A compound according to claim 1 wherein X is ortho-chloro and Y is selected from the group consisting of para-bromo, para-chloro, para-fluoro, and para-trifluoro.

4. A compound according to claim 1 wherein X is ortho-chloro and Y is para-bromo.

5. A compound according to claim 1 wherein X is ortho-chloro and Y is para-chloro.

6. A compound according to claim 1 wherein X is ortho-chloro and Y is para-trifluoromethyl.

7. A compound according to claim 1 wherein X is ortho-chloro and Y is para-fluoro.

8. An insecticidal composition comprising as the active ingredient in combination with a carrier, an insecticidally effective amount of a compound of the following formula:

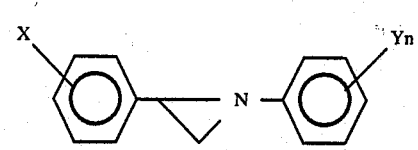

wherein X is selected from the group consisting of halogen in the ortho position, and nitro, and Y is selected from the group consisting of halogen, nitro, trifluoromethyl, and lower alkyl of 1-3 carbon atoms and n is an integer of 1 or 2, provided that when one of X and Y is nitro, the other is halogen.

9. A composition according to claim 8 which is an aqueous composition having a concentration of from about 10-5000 ppm of the active ingredient.

10. A composition of claim 8 wherein the effective amount of the compound is formulated in the form of a solution, suspension, emulsion, powder, or granule.

11. A composition according to claim 9 wherein X is halogen in the ortho position and Y is halogen or trifluoromethyl in the para position.

12. A composition according to claim 11 wherein X is ortho-chloro and Y is para-bromo, para-chloro, para-trifluoromethyl or para-fluoro.

13. A method for the control of insects which comprises administration thereto of an insecticidally effective amount of a composition containing as the effective ingredient a compound of the following formula:

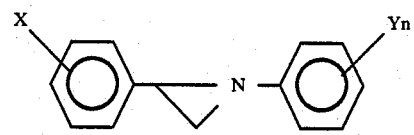

wherein X is selected from the group consisting of, halogen in the ortho position, and nitro, and Y is selected from the group of, halogen, nitro, trifluoromethyl, and lower alkyl of 1-3 carbon atoms, and n is an integer of 1 or 2, provided that when one of X and Y is nitro, the other is halogen.

14. A method according to claim 12 wherein X is halogen in the ortho position and Y is halogen or trifluoromethyl in the para position and n is 1.

15. A method according to claim 13 wherein X is ortho-chloro and Y is para-bromo.

16. A method according to claim 13 wherein X is ortho-chloro and Y is para-chloro.

17. A method according to claim 13 wherein X is ortho-chloro and Y is para-trifluoromethyl.

18. A method according to claim 13 wherein X is ortho-chloro and Y is para-fluoro.

* * * * *